United States Patent [19]

Allen et al.

[11] Patent Number: 4,568,498
[45] Date of Patent: Feb. 4, 1986

[54] (VINYLOXY)CHLOROCYCLOTRIPHOS-PHAZENES

[75] Inventors: Christopher W. Allen, Essex Junction, Vt.; Kolikkara Ramachandran, Oakdale, Minn.; Randall Bright, Crofton, Md.; Jonathan C. Shaw, Burlington, Vt.

[73] Assignee: The United States of America as represented by the Secretary of the Navy, Washington, D.C.

[21] Appl. No.: 605,317

[22] Filed: Apr. 30, 1984

[51] Int. Cl.$^4$ ............................................... C07F 9/24
[52] U.S. Cl. ................................................. 260/927 N
[58] Field of Search .................................... 260/927 N

[56] References Cited

PUBLICATIONS

Harris et al., "Inorg. Chem.", vol 22, (1983), pp. 1812-1817.

Primary Examiner—Anton H. Sutto
Attorney, Agent, or Firm—Robert F. Beers; Arthur A. McGill; Prithvi C. Lall

[57] ABSTRACT

The reaction of the lithium enolate of acetaldehyde, LiOCHCH$_2$, with hexachlorocyclotriphosphazene, N$_3$P$_3$Cl$_6$, lead to the series of (vinyloxy)chlorocyclotriphosphazenes, N$_3$P$_3$Cl$_{6-n}$(OCH=CH$_2$)$_n$(n=1–6). The nongeminal pathway is favored. These materials undergo homopolymerization reaction and can be copolymerized with a wide variety of organic monomers. The resulting polymeric systems incorporate certain properties such as fire retardancy and are chemically bonded to the polymer rather than an additive.

3 Claims, No Drawings

(VINYLOXY)CHLOROCYCLOTRIPHOSPHA- ZENES

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention allows one to incorporate the flame retardant property of the phosphazene into traditional commercial organic polymer. These flame retardants are chemically bonded to the polymer, rather than additives.

(2) Description of the Prior Art

Although there have been extensive investigations into the reactions of amines and more recently of organometallic reagents with cyclophosphazenes, the corresponding reactions with alcohols have received considerably less attention. Detailed studies of the substitution pattern followed in the reactions of phenoxide and the trifluoroethoxide ions with hexachlorocyclotriphosphazene, $N_3P_3Cl_6$, have appeared. Less detailed studies of the reactions of other selected alkoxides with $N_3P_3Cl_6$ have also been carried out. In all cases a nongeminal pathway is preferred. Recently, we have shown that the ambident enolate anions undergo reactions with the hexahalocyclotriphosphazenes $N_3P_3X_6$ (X=F, Cl) to yield the (vinyloxy)pentahalocyclotriphosphenes $N_3P_3X_5OCR=CH_2$. The favorable combination of the hard acid (phosphorus(V)) with the hard base (oxygen) leads to exclusive attack at the oxygen end of the enolate anion and thus provides a route to previously inaccessible vinyl alcohol derivatives.

SUMMARY OF THE INVENTION

The reactions of the lithium enolate of acetaldehyde, $LiOCHCH_2$, with hexachlorocyclotriphosphazene, $N_3P_3Cl_6$, lead to the series of (vinyloxy)chlorocyclotriphosphazenes, $N_3P_3Cl_{6-n}(OCH=CH_2)_n$ (n=1-6). Evidence for the occurrence of all possible geometrical and positional isomers in the series has been obtained from the $^{31}P$ NMR spectra. The principal products are the nongeminal species with comparable amounts of cis and trans isomers being formed. Small amounts of the geminal isomers are also observed. The mono- and pentasubstituted derivatives have been converted to their di-methylamino derivatives, $N_3P_3(OCH=CH_2)_{6-n}[N(CH_3)_2]_n$ (n=1,5).

DESCRIPTION OF THE PREFERRED EMBODIMENTS

The synthesis and characterization of the series of (vinyloxy)chlorcyclotriphosphazenes $N_3P_3Cl_{6-n}(OCH=CH_2)_n$ (n=1-6) is of interest in terms of exploring the substitution pathway of oxygen-based nucleophiles with cyclophosphazenes. These materials are also new organofunctional phosphazenes which can serve as precursors to new monomeric and polymeric phosphazenes derivatives.

For experimental purposes the following was performed: Hexachlorocyclotriphosphazene, $N_3P_3Cl_6$ (Ethyl Corp.), was recrystallized from petroleum ether to a constant melting point of 113° C. n-Butyllithium (1.6M solution in hexane) was obtained from Aldrich. Tetrahydrofuran (THF) (Aldrich) was distilled from sodium-benzophenone ketyl. Petroleum ether (bp 35°-55° C.), benzene, and ethyl acetate (Fisher) were distilled by standard procedures. NMR spectra (in $CDCL_3$) were recorded on a Brucker WM 250 spectrometer operating at 250.1 MHz ($^1H$), 62.9 MHz ($^{13}C$), and 101.2 MHz ($^{31}P$). Tetramethylsilane ($Me_4Si$) was used as internal reference for $^1H$ and $^{13}C$ NMR measurements. for $^{31}P$ NMR, 85% $H_3PO_4$ was used as an external standard. Chemical shifts upfield of the reference are assigned a negative sign. $^{13}C$ and $^{31}P$ NMR spectra were recorded under conditions of broad-band coupling. Infrared (IR) spectra were obtained as their thin films (NaCl disks) on a Beckman IR 20A spectrometer. Mass spectra were recorded on a Perkin-Elmer RMU-6D spectrometer operating at 80 eV. Elemental analyses were performed by Integral Microanalytical Laboratories. The NMR spectra of mixtures were simulated by using a locally modified version of the computer program DNMR3. The original version of the computer program DNMR3 was written by Kleier, D. A.; Binsch, G. J, *Magn. Reson. Relat. Phenom., Proc. Congr. Ampere*, 16th 1970 1971 3, 146. Local modifications are described in Bushweller, C. H.; Bhat, G.; Letendre, L. J.; Burnelle, J. A.; Bilofsky, H. S.; Ruben, H.; Templeton, D. H.; Zalkin, A. J., *J. Am. Chem. Soc.* 1975, 97, 65. The "spectral vector output", i.e., an intensity parameter, of DNMR3 was modified to accommodate the calculation of spectra composed on several overlapping subspectra.

EXAMPLE 1

$N_3P_3Cl_5OCH=CH_2(1)$ and $N_3P_3Cl_4(OCH=CH_2)_2(2)$

A solution of 10.5 g (30.2 mmol) of $N_3P_3Cl_6$ was treated with 70.0 mmol of $LiOCH=CH_2$. A 2-g sample of the product was separated by flash chromatography to yield 0.92 g (44.3% of theory) of $N_3P_3Cl_5OCH=CH_2(1)$. Continued elution from the column yielded 0.70 g (32.80% theory) of a colorless liquid, bp 55°-57° C. (0.02 mmHg). Anal. calculated for $C_4H_6Cl_4N_3O_2P_3(2)$: C, 13.22; H, 1.58; mol wt 361. Found: C, 13.15; H, 1.72; mol wt 361 (mass spectrum).

$^1H$ NMR: $\delta(=POCH=CH_2)=6.6-6.4$ (complex multiplet), $\delta(=POCH=CH_2(trans))=5.2-5.0$ (complex multiplet), $\delta(=POCH=CH_2(cis))=4.9-4.8$ (complex multiplet). $^{31}P$ NMR: for non-geminal isomers $\delta(=PCl_2)=14.8$, $\delta(=PCl(OCH=CH_2))=15.8$ ($^2J_{pp}=67.3$), $\delta(=PCl(OCH=CH_2))=15.6$ ($^2J_{pp}=67.5$); for geminal isomer $\delta(=PCl_2)=24.5$ (d, 2 P) ($^2J_{pp}=68.4$), $\delta(=POCH=CH_2)_2)=-0.6$ (t, 1 P) ($^2J_{pp}=69.0$). IR: 1645 (s, C=C str), 1220 (s, PN str), 1105 (s, PO str), 1030 (m), 925 (m, PCl), 885 (m, PCl), 785 (m, PCl).

EXAMPLE 2

$N_3P_3Cl_3(OCH=CH_2)_3(3)$ and $N_3P_3Cl_2(OCH=CH_2)_4(4)$

The lithium enolate prepared from $n-C_4H_9Li$(45 mL, 72 mmol) and THF (80 mL) was added to a solution of $N_3P_3Cl_6$ (7.5 g, 21.7 mmol) in THF (70 mL) at room temperature. The reaction mixture was stirred for 5 days and worked up as before to give 7.0-g of a pale yellow liquid. A 2.0-g sample of this liquid was purified by using flash chromatography. The following compounds were obtained in succession: $N_3P_3Cl_5OCH=CH_2(1)$, 0.15 g (6.71% of theory);

$N_3P_3Cl_4(OCH=CH_2)_2(2)$, 0.35 g (15.34% of theory). The third compound eluted was distilled under reduced pressure to yield 0.40 g (17.18% of theory) of a colorless liquid, (bp 90° C. (0.05 mmHg). Anal. Calcd for $C_6H_9Cl_3O_3P_3(3)$: C, 19.43; H, 2.43; mol wt 369. Found: C, 19.12; H, 2.41; mol wt 369 (mass spectrum). $^1$H NMR: $\delta(\equiv POCH=CH_2)=6.6–6.4$ (complex multiplet), $\delta(\equiv POCH=CH_2(trans))=5.1–5.0$ (complex multiplet), $\delta(\equiv POCH=CH_2(cis))=4.8–4.6$ (complex multiplet). $^{31}$P NMR: $\delta(\equiv PCl_2)=27.3$, $\delta(\equiv PCl(OCH=CH_2))=18.0$, $\delta(\equiv P(OCH=CH_2)_2)=3.0$. IR: 1640 (s, C=C str), 1230 (s, PN str), 1120 (s, PO str), 1025 (s), 930 (m, PCl), 900 (m, PCl), 790 (m, PCl).

The fourth compound obtained was distilled under reduced pressure to give 0.52 g (21.88% of theory) of a viscous liquid, bp 96° C. (0.05 mmHg). Anal. Calcd for $C_8H_{12}Cl_2N_3O_4P_3(4)$: C, 25.40; H, 3.17; mol wt 377. Found: C, 24.53; H, 2.90; mol wt 377 (mass spectrum).

$^1$H NMR: $\delta(-OCH=CH_2)=6.6–6.4$ (complex multiplet), $\delta(-OCH=CH_2(trans))=5.1–4.9$ (complex multiplet), $\delta(-OCH=CH_2(cis))=4.8–4.7$ (complex multiplet). $^{31}$P NMR: for geminal isomer $\delta(\equiv PCl_2)=28.9$, $\delta(\equiv P(OCH=CH_2)_2)=5.7$ $(^2J_{pp}=75.7)$; for nongeminal isomers $\delta(\equiv PCl(OCH=CH_2))=21.6$, $\delta(\equiv P(OCH=CH_2)_2)=6.1$ $(^2J_{pp}=83.4)$, $\delta(\equiv PCl(OCH=CH_2))=21.4$, $\delta(\equiv P(OCH=CH_2)_2)=6.1$ $(^2J_{pp}=80.6)$. IR: 1645 (s, C=C str), 1230 (s, PN str), 1115 (s, PO str), 1025 (s), 930 (m, PCl), 905 (m, PCl), 785 (m, PCl).

EXAMPLE 3

$N_3P_3Cl(OCH=CH_2)_5(5)$ and $N_3P_3(OCH=CH_2)_6(6)$

The reaction of the lithium enolate prepared from n-$C_4H_9Li$(85 mL, 136 mmol) and THF (160 mL) with $N_3P_3Cl_6$ (6.0 g, 17.2 mmol) in THF (100 mL) was carried out as described above to yield 5.6 g of pale yellow liquid. A 1.0-g sample of this liquid was purified by using flash chromatography with petroleum ether-ethyl acetate (97/3) as the eluant. The first product obtained was a viscous liquid, which was distilled under reduced pressure to give 0.36 g (30.78% of theory) of a colorless liquid, bp 105° C. (0.05 mmHg). Anal. Calcd for $C_{10}H_{15}ClN_3O_5P_3(5)$: C, 31.13; H, 3.89; mol wt 385. Found C, 30.39; H, 3.70; mol wt 385 (mass spectrum).

$^1$H NMR: $\delta(-OCH=CH_2)=6.7–6.4$ (complex multiplet), $\delta(-OCH=CH_2(trans))=5.1–5.0$ (complex multiplet), $\delta(-OCH=CH_2(cis))=4.9–4.6$ (complex multiplet). $^{31}$P NMR: $\delta(\equiv PCl(OCH=CH_2))=23.9$, $\delta(\equiv P(OCH=CH_2)_2)=8.7$ $(^2J_{pp}=85.0)$. $^{13}$C NMR: $PCl(OCH=CH)$ group $\delta(C_d)=141.0$ (d) $(^3J_{PC\alpha}=8.5)$, $\delta(C_\beta)=102.7$ (d) $(^3J_{PC\beta}=12.2)$; $\equiv P(OCH=CH_2)_2$ group $\delta(C_\alpha)=141$ (s), $\delta(C_\beta)=101.8$ (m) $(^2J_{PC\beta}=12.2)$. IR: 1645 (s, C=C str), 1240 (s, PN str) 1110 (s, PO str), 1025 (s), 920 (m, PCl), 860 (m, PCl), 770 (m, PCl).

The next product was distilled under reduced pressure to yield 0.30 g (25.15% of theory) of a viscous liquid, bp 110° C. (0.05 mmHg). Anal. Calcd for $C_{12}H_{18}N_3O_6P_3(6)$: C, 36.64; H, 4.58; mol wt 393. Found: C, 35.88; H, 4.01; mol wt 393 (mass spectrum).

$^1$H NMR: $\delta(-OCH=CH_2)=6.5$ (center of a complex multiplet), $\delta(-OCH=CH_2(trans))=4.9$ (center of a complex multiplet), $\delta(-OCH=CH_2(cis))=4.5$ (center of a complex multiplet, $^{13}$C NMR: $\delta(C_\alpha)=141.6$ (d) $(J_{PC\alpha}=2.4)$, $\delta(C_\beta)=101.3$ (m). $^{31}$P NMR: $\delta(\equiv P(OCH=CH_2)_2)=11.3$ (s). IR: 1645 (s, C=C str),1245 (s, PN str), 1130 (s, PO str), 1010 (s), 865 (m), 810 (m), 760 (m), 690 (m).

EXAMPLE 4

$N_3P_3(OCH=CH_2)(NMe_2)_5(7)$

The reaction of $N_3P_3Cl_5OCH=CH_2(1)$ (2.5 g, 7.1 mmol) with an excess of anhydrous dimethylamine (10.5 g, 233.3 mmol) in chloroform (100 mL) at 0° C. was allowed to proceed for 24 hours. After removal of the solvent, the oily residue was extracted with petroleum ether (250 mL). The amine hydrochloride and petroleum ether were removed, and the remaining liquid was distilled to yield 2.0 g (71.8% of theory) of a colorless liquid, bp 90° C. (0.05 mmHg). Anal. Calcd for $C_{12}H_{33}N_8OP_3(7)$: C, 36.18; H, 8.29; mol wt 398. Found: C, 37.67; H, 8.12; mol wt 398 (mass spectrum).

$^1$H NMR: $\delta(\equiv POCH=CH_2)=6.6$ (m) $(J_{HH}(trans)=13.6, J_{HH}(cis)=5.9, {}^3J_{PH}=7.6)$, $\delta(\equiv POCH=CH_2(trans))=4.6$ (m) $(J_{HH}(trans)=13.6, J_{HH}(gem)=2.2, {}^3J_{PH}=2.0)$, $\delta(\equiv POCH=CH_2(cis))=4.2$ (m) $(J_{HH}(cis)=5.9, J_{HH}(gem)=2.2, {}^4J_{PH}=1.8)$, $\delta(P(OCH=CH_2)(NMe_2))=2.7$ (d) $({}^3J_{PH}=11.8)$, $\delta(\equiv P(NMe_2)_2)=2.6$ (d) $({}^3J_{PH}=11.4)$. $^{31}$P NMR: $\delta(\equiv P(OCH=CH_2)(NMe_2))=23.3$ (t, 1 P) $(^2J_{pp}=47.6)$, $\delta(\equiv P(NMe_2)_2)=27.1$ (d, 2 P) $(^2J_{pp}=50.6)$. $^{13}$C NMR: $\delta(C_\alpha)=142.7$ (d) $(J_{PC}=6.1)$, $\delta(C_\beta)=95.4$ (d) $(J_{PC\beta}=9.8)$, $\delta(\equiv P(OCH=CH_2)$ $(NMe_2))=35.8$ (d) $(J_{PC}=2.4)$, $\delta(\equiv P(NMe_2)_2)=35.6$ (s). IR: 2880 (s, CH str), 1640 (s, C=C str), 1460 (s, $\delta_{as}(CH_3)$), 1275 (s, PN str), 1190 (s), 1120 (s, PO str), 1060 (m), 880 (m, PN), 750 (m), 670 (m).

EXAMPLE 5

$N_3P_3(OCH=CH_2)_5NMe_2(8)$

Anhydrous dimethylamine (10.0 g, 222 mmol) was added to a solution of $N_3P_3Cl(OCH=CH_2)_5(5)$ (0.5 g, 1.4 mmol) in toluene (50 mL) at 0.° C., and the reaction was allowed to proceed as above. The resultant liquid was distilled under reduced pressure to give 0.45 g (87.8% of theory) of a colorless liquid, bp 105° C. (0.05 mmHg). Anal. Calcd for $C_{12}H_{21}N_4O_5P_3(8)$: C, 36.92; H, 5.38; mol wt 350. Found: C, 36.37; H, 5.18; mol wt 350 (mass spectrum).

$^1$H NMR: $\delta(-OCH=CH_2)=6.5$ (center of complex multiplet), $\delta(-OCH=CH_2(trans))=4.9$ (center of complex multiplet), $\delta(-OCH=CH_2(cis))=4.6$ (center of a complex multiplet, $\delta(-NMe_2)=2.7$ (d) $({}^3J_{PH}=12.2)$. $^{13}$C NMR: $\equiv P(OCH=CH_2(NMe_2)$ group $\delta(C_\alpha)=99.6$ (d)$(J_{PC}=11.0, \delta(C_\beta)=142.3$ $(J_{PC\beta}=7.32)$ $\delta(-NMe_2)=36.3$(d) $({}^3J_{PC}=3.7)$; $\equiv P(OCH=CH_2)_2$ group $\delta(C_\alpha)=141.8$ (s), $\delta(C_\beta)=100.4$ (m). $^{31}$P NMR: $\delta(\equiv P(OCH=CH_2)(NMe_2))$ 22.2, $\delta(\equiv P(OCH=CH_2)_2)=11.7$ $(^2J_{pp}=74.6)$. IR: 2920 (m, CH str), 1645 ms, C=C str), 1240 (s, PN str), 1125 (s, PO str), 1010 (s), 920 (m, PN), 870 (m, PN), 810 (m), 770 (m), 695 (m).

There are two possible routes of reaction for an ambident enolate anion leading to derivativization of either the oxygen end or the carbon end of the nucleophile. We have previously shown that the phosphazene is attacked by the oxygen end of the enolate anion in the formation of the monosubstituted derivatives. The $^1$H and $^{13}$C NMR spectra of all the new compounds reported in this investigation closely resemble those of the monosubstituted derivative. In particular, the proton spectra resemble that of vinyl acetate with additional phosphorous coupling and there are no alkyl or carbonyl carbon atoms observed in the $^{13}$C NMR spectra. The NMR spectra of authentic phosphazenes with β- carbonyl functions (the hypothetical product resulting from the attack on the carbon end of the enolate) have recently been reported and differ significantly from the products of the enolate anion reactions. Consequently, we may conclude that the reaction generally leads to the vinyloxy derivatives as shown in equation 1. These materials are stable to air and atmospheric moisture.

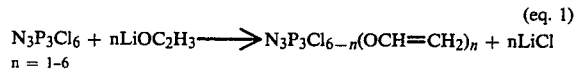

(eq. 1)

$N_3P_3Cl_6 + nLiOC_2H_3 \longrightarrow N_3P_3Cl_{6-n}(OCH=CH_2)_n + nLiCl$ n = 1-6

The monosubstituted derivative, 1, has an $AB_2$ $^{31}P$ NMR spectrum appropriate to the proposed structure. Further characterizational details were previously reported. The chlorine atoms in 1 were removed by the reaction of 1 with dimethylamine to give $N_3P_3[N(CH_3)_2]_5OCH=CH_2$. The $^1H$ and $^{31}P$ NMR spectra of this derivative are consistent with the formulation given above. The fact that 1 can be derivatized leaving the vinyl group intact demonstrates that one can potentially prepare a series of organofunctional phosphazene monomers of the type $N_3P_3X_5OCH=CH_2$ starting with 1.

A mixture of bis isomers, 2, which resisted further chromatographic separation, was isolated. The absence of monomer trisubstituted species was confirmed by mass spectrometry. The observed $^{31}P$ NMR spectrum of clearly showed the existence of all three positional and geometric isomers of the composition $N_3P_3Cl_4(OCH=CH_2)_2$. The NMR parameters for each isomer were estimated from the mixture spectrum and used to simulate the individual spectra. The mixture spectrum was matched to the composite of the individual spectra by varying the contributions of each of the components, thus allowing for calculation of the relative concentration of each species. There was a low-intensity $A_2X$ spectrum in which the A part was in the $≡PCl_2$ chemical shift range while the X part was in the general range found in $N_3P_3(OCH=CH_2)_6$. The $A_2X$ spectrum, with A being $≡PCl_2$, was consistent only with the geminal isomer. Excluding spirocyclic species, this was the first example of a geminal $N_3P_3Cl_4(OR)_2$ species formed in the reactions of nucleophiles derived from alcohols with $N_3P_3Cl_6$. The nongeminal isomers both exhibit $AB_2$ spectra with identical A regions. In the B ($≡PCl(OCH=CH_2)$) region the chemical shifts are slightly different. The relative abundances of each isomer as obtained from the simulation study are 4% geminal and 43 and 53%, respectively, for the two nongeminal isomers. This characterization of the mixture of bis isomers by high-field $^{31}P$ NMR and simulation studies demonstrates the value of this approach in both qualitative and quantitative studies of phosphazene substitution reactions. The proton NMR spectrum of the mixture is, as expected, complex. In the region associated with $H_a$ ($-OCH_a=CH_2$), there is a triplet in low abundance, which is slightly upfield from the $H_a$ resonances for $≡PCl(OCH=CH_2)$ environment. The intensity of the triplet increases as one goes through the $N_3P_3Cl_{6-n}(OCH=CH_2)_n$ series, and so it may be taken as an indicator of the amount of species containing the $≡P(OCH=CH_2)_2$ center in a mixture.

Given the propensity for trans isomer formation observed in the reactions of cyclotriphosphazenes with alkyl- and dialylamines, tert-butyllithium, and the trifluoroethoxide ion, it is tempting to suggest that the isomer in greatest abundance is trans-2,4-$N_3P_3Cl_4(OCH=CH_2)_2$. Any assignment of this type must be considered as tenuous since there is very little knowledge of isomer ratios in the reactions of $N_3P_3Cl_6$ with oxygen bases and a few reactions of cyclotriphosphazenes with nucleophiles such as phenyllithium and the phenoxide ion appear to give the cis isomer predominantly. In the case of the bis(dimethylamino)chlorocyclotriphosphazenes, the $^{31}P$ NMR chemical shift for the $≡PClN(CH_3)_2$ center is more positive for the trans (compared to the cis) isomer. In $N_3P_3Cl_4(OCH=CH_2)_2$, the less abundant nongeminal isomer has the more positive chemical shift for the $≡PCl(OCH=CH_2)$ center. These observations also cast doubt on the suitability of assigning the trans configuration to the more abundant isomer in 2.

The results presented above indicate interesting differences in the reaction pattern in the reactions of $N_3P_3Cl_6$ with $LiOCH=CH_2$ and $NaOCH_2CF_3$. In the latter system, the geminal isomer was not observed and the trans isomer was in significantly greater abundance (trans:cis>5:1). There are not sufficient data to speculate on the reasons for these differences. In particular the roles of the counterion and the solvent bear further investigation.

The sample 3 with stoichiometry $N_3P_3Cl_3(OCH=CH_2)_3$ has a complex $^1H$ NMR spectrum with evidence for the $≡P(OCH=CH_2)_2$ center in small amounts. The $^{31}P$ NMR spectrum of 3 showed evidence for all three isomers (geminal, cis-2,4,6 trans-2,4,6). A doublet of doublets in the $≡P(OCH=CH_2)_2$ region along with a triplet (center lines of doublet of doublets merged) in the $≡PCl_2$ region confirms the presence of the geminal (2,2,4) isomer. The $≡PCl(OCH=CH_2)$ region contains peaks from the geminal isomer, a large singlet corresponding to the cis isomer, and an $AB_2$ pattern assignable to the trans isomer. The overlap of all of these resonances precludes the obtaining of quantitative information concerning isomer ratios. The pattern established at the level of disubstitution is qualitatively maintained, i.e., predominantly nongeminal with traces of geminal product being observed.

The $^{31}P$ NMR spectrum of 4, the tetrasubstituted sample, again indicates the existence of all three isomers. The geminal isomer is in very low abundance and is characterized by an $AX_2$ spectrum with A in the $\delta PCl_2$ and X in the $P(OCH=CH_2)$ region. There are two sets of closely spaced $A_2X$ spectra covering the $≡PCl(OCH=CH_2)_2$ and $P(OCH=CH_2)_2$ regions, which correspond to the nongeminal cis and trans isomers in nearly equal amounts.

The pentasubstituted derivative, 5, exhibits an $AB_2$ $^{31}P$ NMR spectrum, which is approaching $AX_2$. In aminosphosphazene derivatives, materials that appear to be $N_3P_3Cl(NR_2)_5$ are often hydrochlorides of $N_3P_3(NR_2)_6$, so we carried out the reaction of 5 with dimethylamine to yield $N_3P_3N(CH_3)_2(OCH=CH_2)_5$, thus providing chemical structure proof of the proposed formulation of 5.

The $^{31}P$ NMR spectrum of the hexasubstituted material, 6, had the expected singlet in the $≡P(OCH=CH_2)_2$ region. The $^1H$ NMR spectrum showed a curious anomaly in that there was an increase in the number of lines in the $H_a$ region over what was observed in 1. The origins of this complication are unclear, but it does suggest different environments for the exocyclic substituents.

In summary, it has been shown that the reaction of the lithium enolate acetaldehyde with $N_3P_3Cl_6$ leads to the complete series of compounds of the type $N_3P_3Cl_{6-n}(OCH=CH_2)_n$. The nongeminal pathway is favored. This new, and to date most complete, series of organofunctional phosphazenes can be expected to form the basis of extensive new incorporation of cyclophosphazenes into polymeric systems.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A (vinyloxy)chlorocyclotriphosphazene having the formula $N_3P_3Cl_{6-n}(OCH=CH_2)_n$ wherein n represents an integer from 1 to 6.
2. A dimethylamino derivative $N_3P_3(OCH=CH_2)(NMe_2)_5$.
3. A dimethylamino derivative $N_3P_3(OCH=CH_2)_5NMe_2$.

* * * * *